| United States Patent [19] | [11] | 4,329,351 |
|---|---|---|
| Baldwin et al. | [45] | May 11, 1982 |

[54] 2-SUBSTITUTED PROPOXY-3-CYANO-5-RO-PYRIDINES AND INTERMEDIATES

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 80,822

[22] Filed: Oct. 1, 1979

[51] Int. Cl.³ .................... A61K 31/44; C07D 211/90; C07D 211/72
[52] U.S. Cl. .................................. 424/263; 546/288; 546/345
[58] Field of Search ................. 546/288, 345; 424/263

[56] References Cited

U.S. PATENT DOCUMENTS

| 3,632,807 | 1/1972 | Maurer et al. | 546/345 |
|---|---|---|---|
| 3,946,024 | 3/1976 | Fleckenstein et al. | 546/288 |
| 4,000,282 | 12/1976 | Baldwin | 546/288 |
| 4,115,575 | 9/1978 | Frei et al. | 546/288 |
| 4,125,618 | 11/1978 | Baldwin | 546/288 |

FOREIGN PATENT DOCUMENTS 3278 8/1979 Fed. Rep. of Germany ...... 546/288

OTHER PUBLICATIONS

Chem. Abs., vol. 81, 1974, 151944j.

*Primary Examiner*—John M. Ford
*Assistant Examiner*—Robert C. Whittenbaugh
*Attorney, Agent, or Firm*—Daniel T. Szura; Harry E. Westlake, Jr.

[57] ABSTRACT

The present application discloses 2-substituted propoxy-3-cyano-5-RO-pyridines and intermediates therefor. The former compounds have pharmaceutical activity.

12 Claims, No Drawings

2-SUBSTITUTED PROPOXY-3-CYANO-5-RO-PYRIDINES AND INTERMEDIATES

BACKGROUND OF THE INVENTION

The present invention is concerned with 2-substituted-propoxy-3-cyano-5-methoxy, benzyloxy or hydroxypyridines and intermediates.

Disubstituted pyridines having pharmaceutical activity are disclosed in U.S. Pat. Nos. 4,000,282 and 4,125,618. Trisubstituted pyridines are disclosed in U.S. Pat. No. 4,115,575 and EPO publication No. 0,003,278.

Pharmaceutically active trisubstituted pyridines of the present invention have been discovered as well as novel pyridine intermediates.

SUMMARY OF THE INVENTION

3-Cyano-5-substituted oxy-2-(3C$_{3-4}$alkylamino-2-OR-propoxy)-pyridines, their salts and intermediates for their preparation.

DESCRIPTION OF THE PREFERRED EMBODIMENTS

An embodiment of the invention is compounds of the formula

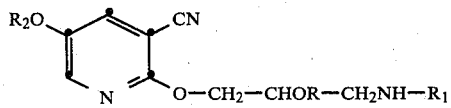

and pharmaceutically acceptable salts thereof wherein R is H or

wherein L is $C_1-C_6$ alkyl such as $CH_3$, isopropyl or hexyl and the like, or phenyl,
$R_1$ is isopropyl or t-butyl and
$R_2$ is $CH_3$,

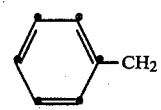

or lower

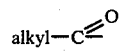

where lower alkyl indicates $C_1-C_6$ alkyl such as methyl, isopropyl, pentyl and the like.

The pharmaceutically acceptable salts are the acid addition salts of the formula I amines. Useful acids for salt formulation include organic as well as inorganic acids. Suitable organic acids are the carboxylic acids having from 2-24 carbon atoms such as fumaric acid, pamoic acid, acetic acid, oxalic acid, maleic acid, succinic acid, pivalic acid, isovaleric acid, lauric acid, tetracosanoic acid, tridecanoic acid, pelargonic acid, tartaric acid, citric acid and the like as well as non-carboxylic acids such as isethionic acid, naphthalene disulfonic acid and the like. Suitable inorganic acids are exemplified by sulfuric acid, phosphoric acid, the hydrohalides such as HCl, HBr, and HI and the like.

The chiral center at the 2-propoxy position confers optical activity on the formula I compounds. The present compounds of formula I thus include the individual isomers, mixtures thereof as well as racemates. The symbols used to designate the isomers include — and +, l and d, L and D, S and R or combinations thereof. Where no specific isomer is designated, all isomers, mixtures thereof and racemates are included. Generally, the S-isomer is preferred.

Preferred compounds of formula I are those where R is H. More preferred formula I compounds are those where R is H and $R_1$ is t-butyl.

The compounds of formula I have pharmacological activity. The compounds are β-adrenergic blocking agents. The compounds also have antihypertensive activity of immediate onset. The compounds are thus useful to treat hypertension in animals, especially humans.

In treating hypertension in human patients, the daily dosage will range from about 1 mg. to about 1000 mg.; preferably from about 10 mg. to about 800 mg. daily; and more preferably from about 50 mg. to about 500 mg. per day.

The compound may be administered by any convenient route e.g. orally, parenterally, intramuscularly and the like using pharmaceutical compositions in a suitable dosage form e.g. tablete, elixirs, solutions or suspensions for oral administration and in sterile solutions for parenteral administration, and the like. These pharmaceutical compositions are prepared using conventional preparation procedures and can contain pharmaceutically acceptable compounding ingredients i.e. diluents, carriers, where required. These pharmaceutical compositions comprise another embodiment of the present invention.

The compounds of Formula I may be prepared by any convenient method. An especially useful process features the coupling of an appropriately substituted oxazolidine with an appropriately substituted 2-halopyridine followed by hydrolysis. This general reaction sequence is known (see e.g. U.S. Pat. No. 4,000,282).

The preparation of the appropriately substituted pyridine is carried out via a series of reactions beginning with the known 5-amino-z-chloro-3-methylpyridine. A number of intermediate compounds are prepared in this sequence. These intermediate compounds are represented by the formula

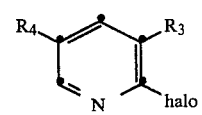

where halo is Br or Cl, preferably Cl, $R_3$ is

$CH_3$, COOH or CN, preferably CN and $R_4$ is F, $C_6H_5-CH_2-O$, $CH_3O$,

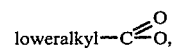

or OH.

The following examples illustrate the preparation of the Formula I and II compounds. All temperatures are in °Celsius.

EXAMPLE 1

(A) Preparation of 2-chloro-5-hydroxy-3-methylpyridine and 2-chloro-5-fluoro-3-methylpyridine To a solution of 5-amino-2-chloro-3-methylpyridine (26.3 g, 0.18 mol) in 12 N HCl (90 mL) and $H_2O$ (157 mL) cooled at $-10°$ C. to $0°$ C. was added dropwise a solution of $NaNO_2$ (13.9 g, 0.20 mol) in $H_2O$ (28 mL). After the addition the solution was stirred for 10 minutes and then 65% $HPF_6$ (90 mL) was added. The resulting mixture was filtered, washed with cold $H_2O$, methanol and $Et_2O$ to yield 61.7 g of diazonium salt, mp $104°-5°$ C. dec. The solid was cautiously added through Gooch tubing to AcOH (425 mL) preheated to $105°$ C. The addition was carried out over 1 hour with noticeable evolution of $N_2$. The solution was concentrated and the residue stirred for 1 hour with 10% NaOH solution (510 Ml). The aqueous solution was extracted with $Et_2O$ (3×), neutralized with concentrated HCl and extracted with $CHCl_3$ (3×). After concentration, the residue was crystallized from methanol/ligroin to yield 14.5 g (56%) of 2-chloro-5-hydroxy-3-methylpyridine, mp $128°-30°$ C. A second crop weighing 2.24 g (8%), mp $126°-8°$ C., was recovered from the mother liquor; $^1H$ NMR ($CDCl_3$) $\delta 2.35$ (3H, s), 7.15 (1H, d, J=3), 7.9 (1H, d, J=3) and 9.4 (1H, bs, exch).

The $Et_2O$ layer (vide supra) was dried, filtered and concentrated. The residue was sublimed at $60°$ C. (1.6 mm) to yield 2.15 g (8%) of 2-chloro-5-fluoro-3-methylpyridine, mp $38°-40°$ C.; $^1H$ NMR ($CFCl_3$) $+129.95$ ppm (1F, d, J=9). The exact mass was 147.0062 (Calcd 147.0065).

(B) Preparation of 2-chloro-5-methoxy-3-methylpyridine

Into a flame dried flask under $N_2$ was placed DMF (150 mL), NaH (50% oil dispersion, 4.0 g, 0.08 mol) and 2-chloro-5-hydroxy-3-methylpyridine (11.7 g, 0.08 mol). The solution was stirred at $0°-5°$ C. until the evolution of $H_2$ ceased and then a solution of $CH_3I$ (5.6 mL, 0.09 mol) in DMF (50 mL) was added dropwise. After the addition, the solution was allowed to stir at room temperature overnight. The resulting slurry was added to $H_2O$ and extracted with $Et_2O$ (3×). The organic layer was concentrated and the residue distilled at $85°$ C. (0.6 mm) to yield 12.8 g of 2-chloro-5-methoxy-3-methylpyridine (95%) as an oil; $^1H$ NMR ($CDCl_3$) $\delta 2.35$ (3H, s), 3.8 (3H, s), 7.1 (1H, d, J=3) and 7.9 (1H, d, J=3); MS m/e (M+) 157.

(C) Preparation of 2-chloro-5-methoxynicotinic Acid

A mixture of 2-chloro-5-methoxy-3-methylpyridine (5.0 g, 0.031 mol), $H_2O$ (400 mL) and $KMnO_4$ (18.8 g, 0.12 mol) was heated at reflux for 1 hour. The resulting mixture was then filtered hot through super-cel, cooled and extracted with $CH_2Cl_2$ (3×). The organic layer was dried, filtered and concentrated to yield 1.1 g of recovered 2-chloro-5-methoxy-3-methylpyridine. The aqueous layer was acidified with 12 N HCl concentrated to a small volume. The solid filtered recrystallized from iso-PrOH/$Et_2O$ to yield 1.6 g (35%) of 2-chloro-5-methoxynicotinic acid, mp $169°-70°$ C.; $^1H$ NMR (DMSO-$d_6$) $\delta 3.95$ (3H, s), 7.85 (1H, d, J=3) and 8.3 (1H, d, J=3); IR (nujol) 1740 cm$^{-1}$.

(D) Preparation of 2-chloro-5-methoxynicotinamide

A solution of 2-chloro-5-methoxynicotinic acid (10.6 g, 0.06 mol) and $SOCl_2$ (140 mL) was heated at reflux for 3 hours. The resulting solution was concentrated and then added to cold ($0°-4°$ C.) aqueous $NH_3$ (1 L). After stirring for 15 minutes, the reaction mixture was concentrated and the residue extracted with hot $H_3CCN$ (3×). The hot $H_3CCN$ solution was filtered and concentrated and to yield 10.6 g (99%) of 2-chloro-5-methoxynicotinamide, mp $129°-32°$ C.; $^1H$ NMR ($CDCl_3$) $\delta 3.85$ (3H, s) 6.6 (2H, bs, exch.), 7.7 (1H, d, J=3) and 8.1 (1H, d, J=3) and 8.1 (1H, d, J=3); IR (nujol) 3330 and 1650 cm$^{-1}$.

(E) Preparation of 2-chloro-5-methoxynicotinonitrile

Into a flame dried flask under $N_2$ was placed triphenylphosphine oxide (12.0 g, 0.04 mol) and $CH_2Cl_2$ (50 mL) and the mixture cooled to $0°-4°$ C. A solution of triflic anhydride (6.75 ml, 0.04 mol) in $CH_2Cl_2$ (80 mL) was added dropwise. After the addition, the solution was stirred for 15 min. and 2-chloro-5-methoxynicotinamide (8.0 g, 0.04 mol) was added portionwise over 15 minutes. The mixture was allowed to warm to room temperature with stirring overnight, poured into saturated $Na_2CO_3$ solution and extracted with $CHCl_3$ (2×). After concentration, the residue was chromatographed on silica gel and the product eluted with $CHCl_3$ to yield 6.2 g (86%) of 2-chloro-5-methoxynicotinonitrile $^1H$ NMR ($CDCl_3$) $\delta 3.9$ (3H, s), 7.5 (1H, d, J=3) and 8.3 (1H, d, J=3); (nujol) 2250 cm$^{-1}$.

(F) Preparation of 2-chloro-5-hydroxynicotinonitrile

A mixture of 2-chloro-methoxynicotinonitrile (3.1 g, 0.018 mol) and $C_5H_5N.HCl$ (90 g) was heated at $200°$ C. with stirring until evolution of gases ceased. After 2 hours, the solution was poured into ice and extracted with $Et_2O$ (3×). The organic layer was dried, filtered, and concentrated to yield 2.0 g (70%) of 2-chloro-5-hydroxynicotinonitrile. An analytical sample of 3-chloro-5-hydroxynicotinonitrile was prepared by recrystallization from $H_2$, mp $182°-4°$ C.; $^1H$ NMR (DMSO-$d_6$) $\delta 7.65$ (1H, d, J=3), 8.0 (1H, d, J=3) and 8.7 (1H, bs, exch); IR (nujol) 2230 cm$^{-1}$; MS m/e M+154.

(G) Preparation of 5-benzyloxy-2-chloronicotinonitrile

To a flame dried flask under $N_2$ was placed 2-chloro-5-hydroxynicotinonitrile (2.0 g, 0.012 mol), DMF (60 mL), NaH (50% oil dispersion, 0.75 g, 0.013 mol) and the mixture cooled to $0°-4°$ C. A solution of benzyl bromide (1.5 mL, 0.013 mol) in DMF (2 mL) was then added and the solution allowed to stir at room temperature overnight. The mixture was poured into $H_2O$ and extracted with $Et_2O$ (3×). The organic layer was concentrated to yield 2.0 g (100%) of 5-benzyloxy-2-chloronicotinonitrile. An analytical sample of 5-benzyloxy-3-chloronicotinonitrile was prepared by trituration with $C_6H_{14}$, mp $114°-15°$ C.; $^1H$ NMR ($CDCl_3$) $\delta 5.2$ (2H, s) 7.4 (5H, s), 7.5 (1H, d, J=3) and 8.35 (1H, d, J=3); IR (nujol) 2220 cm$^{-1}$; MS m/e M+244.

(H) Preparation of (S) 5-benzyloxy-2-(3-tert-butylamino-2-hydroxypropoxy)-nicotinonitrile maleate salt To a flame dried flask under $N_2$ was placed DMF (100 mL), (S)-2-phenyl-3-tert-butyl-5-hydroxymethyloxazolidine, (2.5 g, 0.01 mol) and NaH (50% oil dispersion, 0.5 g, 0.01 mol). The mixture was heated at 90° C. for 10 minutes, then cooled to 35° C. and a solution of 5-benzyloxy-2-chloronicotinonitrile (2.5 g, 0.01 mol) in DMF (25 mL) was added dropwise and allowed to stir at room temperature overnight. The mixture was poured into $H_2O$ and extracted with $Et_2O$ (3×). The organic layer was dried, filtered and concentrated. The residue was treated with 1 N HCl (150 mL) and heated on a steam bath. After 15 minutes, the aqueous solution was cooled, extracted with $Et_2O$ (2×), poured into saturated $Na_2CO_3$ solution and extracted with $CH_2Cl_2$ (3×). After concentration, the residue was crystallized as the maleate salt from isoPrOH/$Et_2O$ to yield 3.3 g (70%) of (S)-5-benzyloxy-2-(3-tert-butylamino-2-hydroxypropoxy)nicotinonitrile maleate mp 124°–6° C.; $^1H$ NMR (DMSO-$d_6$) δ1.3 (9H, s), 3.1 (2H, m), 4.2 (3H, m), 5.2 (2H, s), 6.05 (2H, s, olefinic protons of maleic acid), 7.4 (5H, bs) 8.1 (1H, d, J=3) and 8.25 (1H, d, J=3).

EXAMPLE 2

Preparation of (S) 2-(tert-Butylamino-2-hydroxypropoxy)-5-methoxynicotinonitrile A stirred suspension of 50% sodium hydride in mineral oil (0.22 g., 0.045 mole) in dimethylformamide (35 ml.) was treated under nitrogen with (S) 2-phenyl-3-tert-butyl-5-hydroxymethyloxazolidine (1.06 g., 0.0045 mole) and heated on a steam bath for 20 minutes until hydrogen evolution ceased. After cooling to room temperature a solution of 2-chloro-5-methoxynicotinonitrile (0.70 g., 0.0042 mole) in dimethylformamide (20 ml.) was added dropwise and the mixture stirred at room temperature for 21 hours. The mixture was poured into water (200 ml.) and extracted with ether (3×200 ml.). The combined extracts were washed with water, dried over sodium sulfate and concentrated under reduced pressure. The residue was heated on a steam bath in 1 N HCl (65 ml.) for 30 minutes. After cooling, the mixture was extracted with ether (2×50 ml.), the aqueous layer was carefully poured into saturated sodium carbonate solution (40 ml.) and extracted with $CHCl_3$ (3×75 ml.). The solvent was concentrated under reduced pressure and the residue crystallized from hexane to yield 0.55 g (47%) of (S) 2-(3-tert-butylamino-2-hydroxypropoxy)-5-methoxynicotinonitrile melting at 97°–98.5° C.

Compounds of Formula II where $R_4$ is

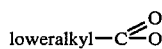

are prepared from the corresponding compounds where $R_4$ is OH by conventional acylation with an appropriate alkanoyl halide or alkanoic acid anhydride. This Formula II intermediate is then converted to the corresponding Formula I compound by substituting this intermediate for 2-chloro-5-methoxynicotinonitrile in substantially the same procedure as Example 2.

Compounds of Formula I where R is

are prepared by conventional acylation of the appropriate Formula I compound where R is H, as illustrated by the following equation:

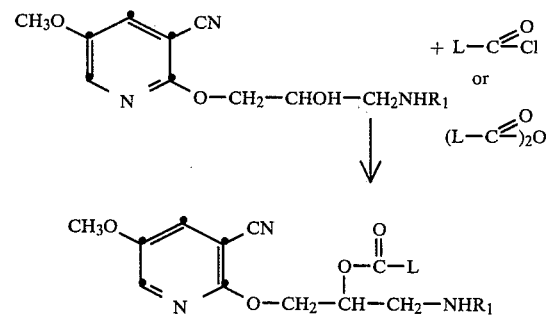

Claims to the invention follow.
What is claimed is:

1. A compound of the formula

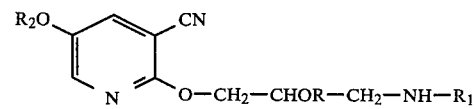

and pharmaceutically acceptable salts thereof wherein R is H or

wherein L is $C_1$–$C_6$ alkyl,
$R_1$ is isopropyl or t-butyl and
$R_2$ is benzyl or

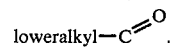

2. Compound of claim 1 wherein R is

3. Compound of claim 1 wherein R is H.
4. Compound of claim 3 wherein $R_1$ is isopropyl.
5. Compounds of claim 3 wherein $R_1$ is t-butyl.
6. Compound of claim 5 wherein $R_2$ is benzyl.
7. Compounds of claim 5 having the S-isomer configuration.
8. A pharmaceutical composition for treating hypertension containing an effective amount of a compound of claim 1 and a carrier.
9. Compounds of the formula

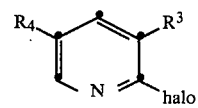

wherein $R_3$ is
—$CH_3$, COOH or CN;
$R_4$ is $CH_3O$, benzyloxy, $C_1$-$C_5$ alkyl  or OH and
halo is Cl or Br
such that when $R_4$ is OH, $R^3$ is other than $CH_3$ or COOH.
10. Compounds of claim 9 wherein $R_3$ is CN and halo is Cl.
11. Compound of claim 10 wherein $R_4$ is OH.
12. A method of immediately reducing hypertension in humans by administering a composition of claim 8 in suitable dosage form.
* * * * *